(12) United States Patent
Bernard et al.

(10) Patent No.: US 10,835,479 B2
(45) Date of Patent: Nov. 17, 2020

(54) SYSTEMS AND METHODS FOR IMPROVING THE APPEARANCE OF THE SKIN

(71) Applicant: L'OREAL, Paris (FR)

(72) Inventors: Anne-Laure Suzanne Bernard, New York, NY (US); Alexandra Jane Elisa Farran, Dayton, NJ (US); Yang Deng, Edison, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/394,862

(22) Filed: Dec. 30, 2016

(65) Prior Publication Data

US 2017/0189321 A1    Jul. 6, 2017

Related U.S. Application Data

(60) Provisional application No. 62/382,178, filed on Aug. 31, 2016, provisional application No. 62/274,078, filed on Dec. 31, 2015.

(51) Int. Cl.
| | | |
|---|---|---|
| A61K 8/02 | (2006.01) | |
| A61K 8/898 | (2006.01) | |
| A61K 8/90 | (2006.01) | |
| A61K 8/81 | (2006.01) | |
| A61Q 19/08 | (2006.01) | |
| A61K 8/25 | (2006.01) | |
| A61K 8/26 | (2006.01) | |
| A61K 8/06 | (2006.01) | |

(52) U.S. Cl.
CPC ............ *A61K 8/898* (2013.01); *A61K 8/0241* (2013.01); *A61K 8/06* (2013.01); *A61K 8/25* (2013.01); *A61K 8/26* (2013.01); *A61K 8/8152* (2013.01); *A61K 8/90* (2013.01); *A61Q 19/08* (2013.01)

(58) Field of Classification Search
None
See application file for complete search history.

(56) References Cited

U.S. PATENT DOCUMENTS

| | | |
|---|---|---|
| 2,463,264 A | 3/1949 | Graenacher et al. |
| 3,635,743 A | 1/1972 | Smith |
| 3,957,713 A | 5/1976 | Jeram et al. |
| 4,693,935 A | 9/1987 | Mazurek |
| 4,725,658 A | 2/1988 | Thayer et al. |
| 4,972,037 A | 11/1990 | Garbe et al. |
| 4,981,902 A | 1/1991 | Mitra et al. |
| 4,981,903 A | 1/1991 | Garbe et al. |
| 5,011,681 A | 4/1991 | Ciotti et al. |
| 5,061,481 A | 10/1991 | Suzuki et al. |
| 5,166,355 A | 11/1992 | Leistner et al. |
| 5,209,924 A | 5/1993 | Garbe et al. |
| 5,219,560 A | 6/1993 | Suzuki et al. |
| 5,236,986 A | 8/1993 | Sakuta |
| 5,237,071 A | 8/1993 | Leistner et al. |
| 5,262,087 A | 11/1993 | Tachibana et al. |
| 5,334,737 A | 8/1994 | Thimineur et al. |
| 5,380,455 A | 1/1995 | Tsuda et al. |
| 5,412,004 A | 5/1995 | Tachibana et al. |
| 5,468,477 A | 11/1995 | Kumar et al. |
| 5,585,091 A | 12/1996 | Pelzer et al. |
| 5,624,663 A | 4/1997 | Deflandre et al. |
| 5,645,609 A | 7/1997 | Andrean et al. |
| 5,665,687 A | 9/1997 | Khayat et al. |
| 5,691,172 A | 11/1997 | Belcour et al. |
| 5,711,940 A | 1/1998 | Kuentz et al. |
| 5,811,487 A | 9/1998 | Schulz, Jr. |
| 5,837,793 A | 11/1998 | Harashima et al. |
| 5,851,517 A | 12/1998 | Mougin et al. |
| 5,879,688 A | 3/1999 | Coury et al. |
| 5,972,329 A | 10/1999 | Chuang et al. |
| 5,977,280 A | 11/1999 | Kadlec et al. |
| 6,045,782 A | 4/2000 | Krog et al. |
| 6,051,216 A | 4/2000 | Barr et al. |
| 6,080,415 A | 6/2000 | Simon |
| 6,093,385 A | 7/2000 | Habeck et al. |
| 6,159,455 A | 12/2000 | Habeck et al. |
| 6,191,301 B1 | 2/2001 | Habeck et al. |
| 6,225,467 B1 | 5/2001 | Esteghamatian et al. |
| 6,238,649 B1 | 5/2001 | Habeck et al. |
| 6,261,544 B1 | 7/2001 | Coury et al. |

(Continued)

FOREIGN PATENT DOCUMENTS

| | | |
|---|---|---|
| CN | 1249170 A | 4/2000 |
| CN | 1397265 A | 2/2003 |

(Continued)

OTHER PUBLICATIONS

Extended European Search Report for counterpart Application No. 15871123.4-1114, dated Sep. 12, 2018.
Non-Final Office Action for copending U.S. Appl. No. 15/087,066, dated May 9, 2018.
Non-Final Office Action for copending U.S. Appl. No. 15/087,115, dated Jul. 27, 2018.
International Preliminary Report on Patentability for counterpart Application No. PCT/US2016/069271, dated Jul. 12, 2018.
International Preliminary Report on Patentability for counterpart Application No. PCT/US2016/069278, dated Jul. 12, 2018.
International Preliminary Report on Patentability for counterpart Application No. PCT/US2016/069294, dated Jul. 12, 2018.
Co-pending U.S. Appl. No. 15/087,115, filed Mar. 31, 2016.
Co-pending U.S. Appl. No. 15/094,259, filed Apr. 8, 2016.
Co-pending U.S. Appl. No. 15/087,066, filed Mar. 31, 2016.

(Continued)

*Primary Examiner* — Susan T Tran
(74) *Attorney, Agent, or Firm* — The Marbury Law Group, PLLC

(57) ABSTRACT

The invention relates to systems and methods for improving the appearance of the skin. The systems comprise 1) a skin-tightening composition comprising at least one thermoplastic elastomer and at least one adhesive polymer; and 2) a long-wear cosmetic composition comprising at least one silicone-polyamide copolymer, at least one silicone film former, and at least one volatile oil. Methods comprise applying the compositions of the systems on to the skin sequentially after a drying period.

20 Claims, 3 Drawing Sheets

(56) References Cited

U.S. PATENT DOCUMENTS

| | | |
|---|---|---|
| 6,284,233 B1 | 9/2001 | Simon et al. |
| 6,338,839 B1 | 1/2002 | Auguste et al. |
| 6,338,855 B1 | 1/2002 | Albacarys et al. |
| 6,342,469 B1 | 1/2002 | Lorant |
| 6,353,076 B1 | 3/2002 | Barr et al. |
| 6,387,355 B2 | 5/2002 | Heidenfelder et al. |
| 6,391,289 B2 | 5/2002 | Heidenfelder et al. |
| 6,423,306 B2 | 7/2002 | Caes et al. |
| 6,436,373 B1 | 8/2002 | Habeck et al. |
| 6,451,295 B1 | 9/2002 | Cai et al. |
| 7,306,771 B2 | 12/2007 | Okawara |
| 7,311,897 B2 | 12/2007 | Ehlis et al. |
| 7,374,771 B2 | 5/2008 | Eversheim et al. |
| 7,470,725 B2 | 12/2008 | Schwertfeger et al. |
| 7,582,719 B1 | 9/2009 | Tan et al. |
| 7,700,084 B2 | 4/2010 | Delage-Grouiller et al. |
| 7,758,848 B2 | 7/2010 | Lu et al. |
| 7,803,877 B2 | 9/2010 | Lion et al. |
| 7,879,316 B2 | 2/2011 | Ferrari et al. |
| 7,993,661 B2 | 8/2011 | Arnaud et al. |
| 8,673,283 B2 | 3/2014 | Bui et al. |
| 8,691,202 B2 | 4/2014 | Yu et al. |
| 10,335,361 B2 | 7/2019 | Cavazzuti et al. |
| 2002/0001570 A1 | 1/2002 | Heidenfelder et al. |
| 2002/0004034 A1 | 1/2002 | Heidenfelder et al. |
| 2002/0016310 A1 | 2/2002 | Habeck et al. |
| 2003/0017124 A1 | 1/2003 | Agostini et al. |
| 2003/0026815 A1 | 2/2003 | Scott et al. |
| 2003/0059392 A1 | 3/2003 | L'Alloret |
| 2003/0068344 A1 | 4/2003 | Ferrari et al. |
| 2003/0091520 A1 | 5/2003 | Livoreil et al. |
| 2003/0157047 A1 | 8/2003 | Lennon et al. |
| 2003/0158363 A1 | 8/2003 | Nakanishi |
| 2003/0235553 A1* | 12/2003 | Lu .................. A61Q 1/02 424/70.122 |
| 2004/0013624 A1 | 1/2004 | Mateu et al. |
| 2004/0137028 A1 | 7/2004 | de la Poterie |
| 2004/0191191 A1 | 9/2004 | Ehlis et al. |
| 2004/0192832 A1 | 9/2004 | Cordier |
| 2004/0197284 A1 | 10/2004 | Auguste |
| 2005/0008667 A1 | 1/2005 | Liechty et al. |
| 2005/0013782 A1 | 1/2005 | Goppel et al. |
| 2005/0069564 A1 | 3/2005 | Eversheim et al. |
| 2005/0183511 A1 | 8/2005 | Giron |
| 2005/0186166 A1 | 8/2005 | Patil et al. |
| 2005/0239950 A1 | 10/2005 | Martin et al. |
| 2005/0244974 A1 | 11/2005 | Garcia-Franco et al. |
| 2005/0287088 A1 | 12/2005 | Guiramand et al. |
| 2006/0034875 A1 | 2/2006 | Nakanishi et al. |
| 2006/0193801 A1 | 8/2006 | Blin et al. |
| 2006/0193803 A1 | 8/2006 | Farcet |
| 2007/0041928 A1 | 2/2007 | Chen et al. |
| 2007/0055014 A1* | 3/2007 | Lu .................. A61K 8/37 525/64 |
| 2007/0140991 A1 | 6/2007 | Maitra et al. |
| 2007/0224147 A1 | 9/2007 | Richard |
| 2007/0258923 A1 | 11/2007 | Bui et al. |
| 2007/0258924 A1 | 11/2007 | Bui et al. |
| 2007/0258934 A1 | 11/2007 | Bui et al. |
| 2008/0102084 A1 | 5/2008 | McDermott |
| 2008/0102049 A1* | 5/2008 | McDermott ......... A61K 8/26 424/64 |
| 2008/0107615 A1 | 5/2008 | Keene et al. |
| 2008/0233075 A1 | 9/2008 | Sokolinsky et al. |
| 2009/0074689 A1 | 3/2009 | Auguste |
| 2010/0009931 A1 | 1/2010 | Laboreau et al. |
| 2010/0197805 A1* | 8/2010 | Cassin .................. A61K 8/31 514/772.1 |
| 2011/0020263 A1 | 1/2011 | Ilketi et al. |
| 2011/0098424 A1 | 4/2011 | Carpentier et al. |
| 2011/0123650 A1 | 5/2011 | Kimura |
| 2011/0243864 A1 | 10/2011 | Farcet et al. |
| 2013/0028851 A1 | 1/2013 | Fontaine et al. |
| 2013/0078209 A1 | 3/2013 | Yu et al. |
| 2013/0164235 A1 | 6/2013 | Lebre-Lemonnier et al. |
| 2013/0202546 A1* | 8/2013 | Howell .............. A61K 8/8152 424/70.16 |
| 2013/0236406 A1 | 9/2013 | Tong et al. |
| 2013/0236407 A1 | 9/2013 | Tong et al. |
| 2013/0236408 A1 | 9/2013 | Bui et al. |
| 2013/0236409 A1 | 9/2013 | Bui et al. |
| 2014/0004073 A1 | 1/2014 | Yu et al. |
| 2015/0272853 A1 | 10/2015 | Kishina et al. |
| 2015/0366789 A1 | 12/2015 | Mei et al. |
| 2016/0000670 A1 | 1/2016 | Pesaro et al. |
| 2018/0015023 A1* | 1/2018 | Bernard ................. A61K 8/25 |
| 2019/0029930 A1 | 1/2019 | Deng et al. |
| 2019/0029943 A1 | 1/2019 | Bernard et al. |
| 2019/0091130 A1 | 3/2019 | Farran et al. |
| 2019/0091134 A1* | 3/2019 | Bernard ................. A61K 8/19 |

FOREIGN PATENT DOCUMENTS

| | | |
|---|---|---|
| CN | 1415280 A | 5/2003 |
| CN | 1490500 A | 4/2004 |
| CN | 1504488 A | 6/2004 |
| CN | 1572287 A | 2/2005 |
| CN | 101084864 A | 12/2007 |
| CN | 101843569 A | 9/2010 |
| CN | 103037836 A | 4/2013 |
| CN | 103153279 A | 6/2013 |
| DE | 19726184 A1 | 12/1998 |
| DE | 19746654 A1 | 2/1999 |
| DE | 19755649 A1 | 6/1999 |
| DE | 19855649 A1 | 6/2000 |
| DE | 10162844 A1 | 7/2003 |
| EP | 0669323 A1 | 8/1995 |
| EP | 0832642 A2 | 4/1998 |
| EP | 0893119 A1 | 1/1999 |
| EP | 3967200 A1 | 12/1999 |
| EP | 1008586 A1 | 6/2000 |
| EP | 1027883 A2 | 8/2000 |
| EP | 1133980 A2 | 9/2001 |
| EP | 1133981 A2 | 9/2001 |
| EP | 1300137 A2 | 4/2003 |
| FR | 2679771 A1 | 2/1993 |
| FR | 2785530 A1 | 5/2000 |
| FR | 2860155 A1 | 4/2005 |
| FR | 2863493 A1 | 6/2005 |
| FR | 2887446 A1 | 12/2006 |
| FR | 2951641 A1 | 4/2011 |
| FR | 2983717 A1 | 6/2013 |
| GB | 2303549 A | 2/1997 |
| JP | 56-020515 A | 2/1981 |
| JP | 56020515 A * | 2/1981 |
| JP | H2-223508 A | 9/1990 |
| JP | H11-502228 A | 2/1999 |
| JP | 2000-086491 A | 3/2000 |
| JP | 2002-302421 A | 10/2002 |
| JP | 2002-537314 A | 11/2002 |
| JP | 2004-277299 A | 10/2004 |
| JP | 2006-143714 A | 6/2006 |
| JP | 2006-213717 A | 8/2006 |
| JP | 2007-023037 A | 2/2007 |
| JP | 2007-506708 A | 3/2007 |
| JP | 2007-203491 A | 8/2007 |
| JP | 2007-297391 A | 11/2007 |
| JP | 2009-536185 A | 10/2009 |
| JP | 2014-172909 A | 9/2014 |
| WO | 93/04665 A1 | 3/1993 |
| WO | 01/32737 A1 | 5/2001 |
| WO | 03/042221 A1 | 5/2003 |
| WO | 2004/006878 A1 | 1/2004 |
| WO | 2004/024798 A1 | 3/2004 |
| WO | 2004/085412 A2 | 10/2004 |
| WO | 2005/030155 A1 | 4/2005 |
| WO | 2005/030158 A1 | 4/2005 |
| WO | 2005/058269 A1 | 6/2005 |
| WO | 2005/100444 A1 | 10/2005 |
| WO | 2006/032741 A1 | 3/2006 |
| WO | 2006/034982 A1 | 4/2006 |
| WO | 2006/034985 A1 | 4/2006 |
| WO | 2006/034991 A1 | 4/2006 |
| WO | 2006/034992 A1 | 4/2006 |

(56) References Cited

FOREIGN PATENT DOCUMENTS

| WO | 2006/035000 A1 | 4/2006 |
|---|---|---|
| WO | 2006/035007 A1 | 4/2006 |
| WO | 2008/075283 A2 | 6/2008 |
| WO | 2012/030984 A2 | 3/2012 |
| WO | 2013/190136 A2 | 12/2013 |
| WO | 2014/143757 A1 | 9/2014 |
| WO | 2014/167543 A1 | 10/2014 |
| WO | 2015/091513 A1 | 6/2015 |
| WO | 2016/100690 A1 | 6/2016 |

OTHER PUBLICATIONS

Counterpart International Application No. PCT/US2015/066420, filed Dec. 17, 2015.
Counterpart International Application No. PCT/US2015/066516, filed Dec. 17, 2015.
Counterpart International Application No. PCT/US2015/066510, filed Dec. 17, 2015.
Counterpart International Application No. PCT/US2015/066513, filed Dec. 17, 2015.
Burnett, Draft Report on Nylon, Cosmetic Ingredient Review, Jun. 11, 2012, pp. 1-40.
International Search Report and Written Opinion for counterpart PCT/US2015/066420, dated Feb. 26, 2016.
International Search Report and Written Opinion for counterpart PCT/US2015/066510, dated Feb. 26, 2016.
International Search Report and Written Opinion for counterpart PCT/US2015/066513, dated Feb. 26, 2016.
International Search Report and Written Opinion for counterpart PCT/US2015/066516, dated Mar. 3, 2016.
International Search Report and Written Opinion for counterpart PCT/US2016/069278, dated Mar. 13, 2017.
Mallard Creek Polymers, "Understanding the Glass Transition Temperature," Nov. 10, 2015 [retrieved from http://www.mcpolymers.com/library/understanding-the-glasstransition-temperature, Feb. 12, 2017.
International Search Report and Written Opinion for counterpart PCT/US2016/069271, dated Mar. 16, 2017.
International Search Report and Written Opinion for counterpart PCT/US2016/069294, dated Mar. 24, 2017.
Non-Final Office Action for co-pending U.S. Appl. No. 15/094,259, dated Apr. 20, 2017.
Final Office Action for copending U.S. Appl. No. 15/087,115, dated Jan. 26, 2018.
Final Office Action for copending U.S. Appl. No. 15/094,259, dated Jan. 25, 2018.
Final Office Action for copending U.S. Appl. No. 15/087,066, dated Jan. 22, 2018.
International Preliminary Report on Patentability for PCT/US2015/066420, dated Jun. 29, 2017.
International Preliminary Report on Patentability for PCT/US2015/066516, dated Jun. 29, 2017.
International Preliminary Report on Patentability for PCT/US2015/066510, dated Jun. 29, 2017.
International Preliminary Report on Patentability for PCT/US2015/066513, dated Jun. 29, 2017.
Non-Final Office Action for co-pending U.S. Appl. No. 15/081,115, dated Jul. 20, 2017.
Non-Final Office Action for co-pending U.S. Appl. No. 15/087,066, dated Sep. 15, 2017.
Sigma-Aldrich specification sheet for poly(dimethylsiloxane-co-methylhydroslloxane) trimethylsilyl terminated (1 page, accessed Sep. 11, 2017, http://www.sigmaaldrich.com/catalog/product/aldrich/482196?lang=en&region=US).
Final Office Action for copending U.S. Appl. No. 15/087,066, dated Oct. 25, 2018.
Notice of Allowance for copending U.S. Appl. No. 15/087,115, dated Feb. 1, 2019.
Non-Final Office Action for co-pending U.S. Appl. No. 15/094,259, dated Mar. 8, 2019.
Co-pending U.S. Appl. No. 16/367,568, entitled: "Compositions for Removing Cosmetic Films," Inventors: Anne-Laure Suzanne Bernard et al., filed Mar. 28, 2019.
Non-Final Office Action for co-pending U.S. Appl. No. 15/531,122, dated May 17, 2019.
Non-Final Office Action for co-pending U.S. Appl. No. 15/537,130, dated Aug. 20, 2019.
Gold et al., "Here's What you Need to Know About Titanium Dioxide and Zinc Oxide Sunscreens," Women's Health, Titanium Dioxide and Zinc Oxide—What is Mineral Sunscreen, accessed Aug. 13, 2019, pp. 1-10.
Final Office Action for co-pending U.S. Appl. No. 15/537,122, dated Aug. 9, 2019.
Extended European Search Report for counterpart Application No. 16882678.2-1114, dated May 17, 2019.
European Office Action for counterpart Application No. 15871083.0-1114, dated Aug. 20, 2019.
European Office Action for counterpart Application No. 15871124.2-1114, dated Aug. 20, 2019.
European Office Action for counterpart Application No. 15871123.4-1114, dated Aug. 12, 2019.
Brazilian Office Action for counterpart Application No. BR112017012615-0, dated Aug. 27, 2019, with Translation.
Non-Final Office Action for co-pending U.S. Appl. No. 15/087,066, dated Jun. 20, 2019.
Non-Final Office Action for co-pending U.S. Appl. No. 15/537,099, dated Jul. 10, 2019.
Non-Final Office Action for counterpart Japanese Application No. 2017-532869, dated Jan. 6, 2020.
Non-Final Office Action for counterpart Japanese Application No. 2017-532876, dated Jan. 6, 2020.
Translated Japanese First Office Action for counterpart Application No. 2017-532891, dated Dec. 2, 2019.
Translation of Japanese Office Action for counterpart Application No. 2018-534805, dated Dec. 9, 2019.
Translation of Japanese Office Action for counterpart Application No. 2017-532875, dated Dec. 9, 2019.
Final Office Action for co-pending U.S. Appl. No. 15/537,130, dated Feb. 7, 2020.
Non-Final Office Action for co-pending U.S. Appl. No. 15/537,122, dated Feb. 24, 2020.
Translated First Office Action for counterpart CN Application No. 201580076414.5, dated Jan. 10, 2020.
Search Report for counterpart CN Application No. 201580076414.5, dated Jan. 2, 2020.
Final Office Action for co-pending U.S. Appl. No. 15/537,099, dated Nov. 6, 2019.
Translation of First Office Action for counterpart CN Application No. 201580076415X, dated Oct. 23, 2019.
Search Report for counterpart CN Application No. 201580076415X, dated Oct. 23, 2019.
Translation of First Office Action for counterpart CN Application No. 2015800761946, dated Oct. 24, 2019.
Search Report for counterpart CN Application No. 2015800761946, dated Oct. 24, 2019.
Translated First Office Action for counterpart CN Application No. 2015800764427, dated Nov. 4, 2019.
Search Report for counterpart CN Application No. 2015800764427, dated Nov. 4, 2019.
Non-Final Office Action for copending U.S. Appl. No. 15/094,259, dated Apr. 3, 2020.
Brazilian Office Action for counterpart Application No. BR112017012836-5, dated Aug. 27, 2019, with Translation.
Brazilian Office Action for counterpart Application No. BR112017012667-2, dated Aug. 27, 2019, with Translation.
Brazilian Office Action for counterpart Application No. BR112017012663-0, dated Sep. 6, 2019, with Translation.
Translation of Decision of Refusal for counterpart JP Application No. 2017-532876, dated Jun. 1, 2020.
Translated First Office Action for counterpart CN Application No. 201680081974.4, dated Jun. 10, 2020.

(56) References Cited

OTHER PUBLICATIONS

Translated Second Office Action and Supplemental Search Report for counterpart CN Application No. 201580076415.X, dated Jun. 17, 2020.
Translated Decision of Rejection for counterpart JP Application No. 2017-532891, dated Jun. 22, 2020.
Final Office Action for co-pending U.S. Appl. No. 15/094,259, dated Sep. 19, 2019.
Bornholtz, "8 Foundation Hacks You Need to Know," Women's Health, available online Nov. 17, 2014.
Non-Final Office Action for co-pending U.S. Appl. No. 15/394,862, dated Oct. 3, 2019.
Final Office Action for co-pending U.S. Appl. No. 15/087,066, dated Oct. 21, 2019.
Non-Final Office Action for copending U.S. Appl. No. 15/537,099, dated May 14, 2020.
Non-Final Office Action for copending U.S. Appl. No. 15/537,112, dated Jun. 2, 2020.
Brazilian Office Action and translated Written Opinion for counterpart Application No. BR112018013350, dated Feb. 28, 2020.
Non-Final Office Action for copending U.S. Appl. No. 16/367,568, dated Jul. 17, 2020.
European Office Action for counterpart Application No. 16 882 678.2-1112, dated Jul. 20, 2020.
Translated Chinese Office Action for counterpart Application No. 201580076442-7, dated Jul. 30, 2020.
Translated Japanese Office Action for counterpart Application No. 2017-532875, dated Aug. 3, 2020.

\* cited by examiner

SYSTEMS AND METHODS FOR IMPROVING THE APPEARANCE OF THE SKIN This application claims priority to U.S. Provisional Patent Application No. 62/274,078, filed Dec. 31, 2015, and U.S. Provisional Application No. 62/382,178, filed Aug. 31, 2016.

TECHNICAL FIELD

The disclosure relates systems containing a skin-tightening film and a long-wear cosmetic composition, and the use thereof for improving the appearance of the skin.

BACKGROUND

Many cosmetic compositions, including pigmented cosmetics such as foundations, concealers, lipsticks, mascaras, and other cosmetic and sunscreen compositions have been developed for longer wear and transfer resistance properties. This is accomplished by the use of compositions that form a film after application. Such compositions generally contain volatile solvents, which evaporate on contact with the skin or other keratinous tissue, leaving behind a layer comprising waxes and/or resins, pigments, fillers, and actives. However, these compositions tend to be uncomfortable for the wearer as the composition remains on the skin or other keratinous tissue as a brittle or non-flexible film. Such compositions may not be pliable or soft, and they may not be comfortable to wear. There may also be a tendency for such compositions to flake off because of poor adherence to the skin or other keratinous tissue. Furthermore, such compositions have a tendency to be tacky, resulting in poor application, spreadability and wear characteristics The use of fatty phases based on silicone oils makes it possible to obtain cosmetic compositions with long staying power when the oils are non-volatile or relatively non-volatile, namely good staying power over time of the color (no color change and no fading), and transfer-resistant compositions when the silicone oils are volatile, namely compositions that do not deposit onto a support such as a glass, a cup, a fabric or a cigarette, when placed in contact with the film of makeup However, there remains a need for cosmetic treatment combining a skin-tightening film and a long-wear cosmetic composition to improve the appearance of the skin. As such, there is a consumer desire for topical cosmetic formulations that are effective at reducing the appearance of skin imperfections while simultaneously reducing the appearance of wrinkles.

SUMMARY

The disclosure relates to systems and methods for improving the appearance of the skin.

In various embodiments, the disclosure relates to systems comprising: (1) a skin-tightening composition comprising (a) at least one amorphous hydrocarbon block copolymer of styrene and monomers of hydrocarbon containing 2 to 5 carbon atoms and comprising one or two ethylenic unsaturations, and having a first $T_g$ below about 0° C., and a second $T_g$ greater than about 25° C., (b) at least one adhesive film-forming polymer chosen from polymer particles of $C_1$-$C_4$ alkyl(methacrylate)polymer, stablilized in a non-aqueous dispersion, and (c) at least one filler; and (2) a long-wear cosmetic composition comprising at least one silicone-polyamide copolymer, at least one silicone film former, and at least one volatile oil.

In further embodiments, the disclosure relates to methods for improving the appearance of the skin, said methods comprising applying to the skin a system comprising: (1) a skin-tightening composition comprising (a) at least one amorphous hydrocarbon block copolymer of styrene and monomers of hydrocarbon containing 2 to 5 carbon atoms and comprising one or two ethylenic unsaturations, and having a first $T_g$ below about 0° C., and a second $T_g$ greater than about 25° C., (b) at least one adhesive film-forming polymer chosen from polymer particles of $C_1$-$C_4$ alkyl (methacrylate)polymer, stablilized in a non-aqueous dispersion, and (c) at least one filler; and (2) a long-wear cosmetic composition comprising at least one silicone-polyamide copolymer, at least one silicone film former, and at least one volatile oil.

DESCRIPTION OF THE DRAWINGS

Implementation of the present technology will now be described, by way of example only, with reference to the attached figures, wherein.

Figure 1:
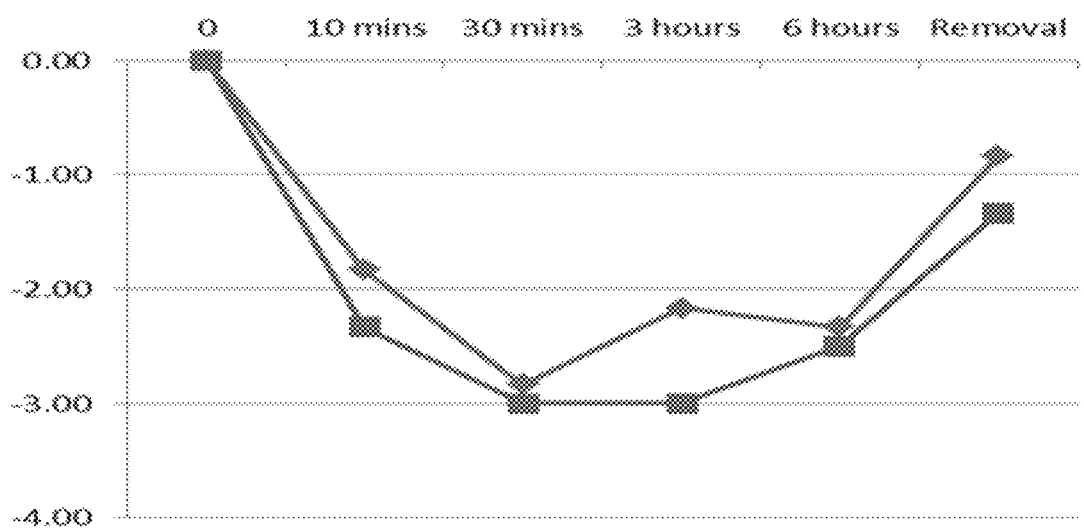
FIG. 1 demonstrates compatibility between an exemplary skin-tightening composition according to an embodiment of the disclosure and long wear foundation, and effect on under-eye bags.

It should be understood that the various aspects provided by the figures are not limited to the arrangements and instrumentality shown in the figures.

DETAILED DESCRIPTION

In various embodiments, the disclosure relates to systems and methods for improving the appearance of the skin. According to various embodiments, the systems according to the disclosure comprise a skin-tightening composition capable of forming a film on the skin, and a long wear cosmetic composition, and methods comprising applying the skin-tightening composition onto the skin before or after applying the long-wear cosmetic composition onto the skin.

The systems and methods may be effective at reducing the appearance of skin imperfections. In various embodiments, the systems and methods may improve the appearance of wrinkles in the skin by forming a film on the skin that has a Young Modulus greater than that of skin, and thus has the capability of tightening the skin, while reducing the appearance of skin imperfections such as pimples, scars, age-spots, uneven skin tone, and the like, for example by blurring or hiding such skin imperfections.

As used herein, "long wear" compositions refer to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (including lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Film former" or "film forming agent" as used herein means a polymer that, after dissolution in at least one solvent (such as, for example, water and organic solvents), leaves a film on the substrate to which it is applied, for example, once the at least one solvent evaporates, absorbs and/or dissipates on the substrate.

The term "long-lasting" means that the film lasts for at least about 6 hours, such as at least about 12 hours, at least about 24 hours, at least about 48 hours, or at least about 72 hours, after the film is formed on the skin.

As used herein, the term "lasting" it is meant to convey that the film is substantially intact in place on the skin.

As used herein, the term "forms quickly" with reference to a skin-tightening film means that the film forms within less than about 20 minutes, such as less than about 15 minutes, or less than about 10 minutes, after the skin-tightening composition is applied to the skin.

As used herein, the term "blur" with regard to skin imperfections means that the visual appearance of the imperfection is less noticeable.

As used herein, the term "tighten" means that the film contracts in a manner that skin has a tighter feel to the user, and that reduces the visual appearance of wrinkles in the skin.

As used herein, the term "soft focus" means that the visual appearance of the skin is more homogenous and matte, leading to the blurring or hiding of skin imperfections.

As used herein, "durable" means the film will not easily rub off, or will not be removed by sweat, water, makeup, lotions, or the like, such that the film will remain substantially intact until removed by the user.

Systems

The systems according to embodiments of the disclosure comprise a long-wear cosmetic composition and a skin-tightening composition capable of forming a film on the skin.

Long-Wear Cosmetic Composition

According to various embodiments, the long-wear cosmetic composition useful in the systems and methods described herein may be chosen from make-up, foundation, and concealer formulations. In various embodiments, the formulations may be chosen from liquid, cream, gel, mousse, stick, solid, and powder formulations.

The long-wear cosmetic composition contains at least one silicone-polyamide copolymer, at least one silicone film former, and at least one volatile oil. In at least some embodiments, the cosmetic compositions are free or substantially free of non-volatile solvent.

The long-wear cosmetic composition of this invention is described in U.S. Pat. No. 7,879,316, which is incorporated herein by reference.

Silicone-polyamide copolymers useful herein include dimethicone copolymers and dimethicone crosspolymers, preferably, a nylon-611/dimethicone copolymer. Silicone-polyamide copolymers are described in U.S. Pat. Nos. 6,451,295, 6,353,076 and 6,051,216, all of which are incorporated herein by reference.

The amount of silicone-polyamide copolymer used in the invention composition is not particularly limited, and may range from, for example, 0.1-25% by weight and more based on total weight of the composition, preferably 0.5-10% including 2, 3, 4, 5, 6, 7, 8, and 9% and all values and subranges there between. The amount of copolymer may be varied depending upon the form of the invention composition desired which, in view of this disclosure, is within the skill of the ordinary artisan.

The silicone film former of the long-wear cosmetic composition can be chosen from silsesquioxane, polyalkylsilsesquioxane, polymethylsilsesquioxane, siloxysilicate, trialkylsiloxysilicate, and trimethylsiloxysilicate.

The silicone film former may be a polymethylsilsesquioxane film former such as Belsil PMS MK, also referred to as Resin MK, available from Wacker Chemie. The weight-average molecular weight of this polymer has been estimated to be 10,000. It is believed that the polymers are in a "cage" and "ladder" configuration, as exemplified in the figures below. The majority of the polymer is in the "ladder" configuration. The ethoxy groups are generally present in an amount of 4.5% by weight and the mole percent is generally 7% (silicone units). As ethoxy groups may react with water, a small and variable amount of SiOH may also be present in the polymer. Another non-limiting example of the at least one polymethylsilsesquioxane film former suitable for use in the present invention is KR-220L, which is available from SHIN-ETSU.

Other non-limiting examples of the at least one polymethylsilsesquioxane film former that may be useful in the practice of the invention include KR-242A (which is comprised of methyl T units (98%) and dimethyl D units (2%) and has Si—OH end units) and KR-251 (which is comprised of methyl T units (88%) and dimethyl D units (12%) and has Si—OH end units), both of which are available from SHIN-ETSU.

Acceptable silicone film formers are known in the art and include, but are not limited to, those disclosed in U.S. patent application publication no. 2004/0170586, the entire contents of which is hereby incorporated by reference.

Non-limiting representative examples of acceptable film formers include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

Suitable examples of acceptable liposoluble polymers include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Acceptable film formers also include water soluble polymers such as, for example, high molecular weight cross-linked homopolymers of acrylic acid, and Acrylates/C10-30 Alkyl Acrylate Crosspolymer, such as the Carbopol® and Pemulen®; anionic acrylate polymers such as Salcare® AST and cationic acrylate polymers such as Salcare® SC96; acrylamidopropylttrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof.

Depending on the application, the concentration of the at least one polymethylsilsesquioxane film former in the presently claimed composition may vary considerably. One of skill in the art will be able to determine routinely the amount of the at least one polymethylsilsesquioxane film former depending on the desired application.

In another embodiment, the silicone film former may be chosen from siloxysilicates. Preferably, the siloxysilicate is trimethylsiloxysilicate, which may or may not be in powder form. Trimethylsiloxysilicate (TMS) is commercially available from General Electric under the tradename SR1000 and from Wacker under the tradename TMS 803. TMS is also commercially available from Dow Chemical in a solvent, such as for example, cyclomethicone. However, according to the present invention, TMS may be used in the form of 100% active material, that is, not in a solvent.

Further non-limiting examples of the silicone film formers include silicone/(meth)acrylate copolymers, such as those as described in U.S. Pat. Nos. 5,061,481, 5,219,560, and 5,262,087, the disclosures of which are hereby incorporated by reference. Still further non-limiting examples of silicone film formers are non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545, or acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

Other non-limiting examples of silicone film formers suitable for use in the present invention are silicone esters comprising units of formulae (XIV) and (XV), disclosed in U.S. Pat. Nos. 6,045,782, 5,334,737, and 4,725,658, the disclosures of which are hereby incorporated by reference.

According to preferred embodiments, the silicone film former is present in the composition in an amount ranging from 0.1% to 30% by weight relative to the total weight of the composition. Preferably, the silicone film former is present in an amount ranging from 0.5% to 20% by weight relative to the total weight of the composition, and more preferably from 1% to 10%. One of ordinary skill in the art will recognize that the silicone film former of the present invention may be commercially available, and may come from suppliers in the form of a dilute solution. The amounts of the silicone film former disclosed herein therefore reflect the weight percent of active material.

Colorants

The long-wear cosmetic composition may further comprise a colorant component. In various embodiments, the colorant component comprises organic pigments. In further embodiments, the colorant component consists essentially of organic pigments. In yet further embodiments, the colorant component consists of organic pigments.

The organic pigments may be present in the cosmetic composition in an amount ranging from about 2% to about 90%, such as about 5% to about 80%, by weight, relative to the cosmetic composition. In embodiments where there is no, or substantially no, solvent in the cosmetic composition, the amount of organic pigment may be higher. For example, the total amount of organic pigments may be about 50% to about 90% by weight, relative to the cosmetic composition. In embodiments where the cosmetic composition comprises one or more solvents, the amount of organic pigment may be lower. For example, the total amount of organic pigments may be about 10% to about 20% by weight, relative to the cosmetic composition.

By way of non-limiting example only, organic pigments that may be used include nitroso, nitro, azo, xanthene, pyrene, quinoline, anthraquinone, triphenylmethane, fluorane, phthalocyanin, metal complex, isoindolinone, isoindoline, quinacridone, perinone, perylene, diketopyrrolopyrrole, indigo, thioindigo, dioxazine, triphenylmethane and quinophthalone compounds. For example, the organic pigments may be chosen from carmine lake, carbon black, aniline black, azo yellow, quinacridone, phthalocyanine blue, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

Solvents

The long-wear cosmetic composition according to the present invention also comprises at least one volatile oil, preferably a silicone volatile oil, a hydrocarbon volatile oil, or a mixture thereof.

In various embodiments, the long-wear cosmetic compositions comprise at least one volatile oil, and optionally a non-volatile oil. The cosmetic compositions may, in at least certain embodiments, comprise volatile and non-volatile oils.

According to the invention, when volatile oils are present, these volatile oils permit an easier application of the composition on the skin, lips or keratinous fibers.

According to one embodiment, the composition may contain one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94.degree. C. Preferably, the volatile silicone oils have a flash point of at least 40° C.

Examples of other silicone oils that may be used in the invention include non-volatile linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

Further, a volatile linear silicone oil may be employed in the compositions of the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

The volatility of the solvents/oils can be determined using the evaporation speed as set forth in U.S. Pat. No. 6,338,839.

According to other preferred embodiments, the composition may contain one or more non-silicone volatile oils and may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched 8 to 16 carbon-atom alkanes, such as isoalkanes (also known as isoparaffins), isododecane, isodecane, isohexadecane, and for example, the oils sold under the trade names of Isopar or Permethyl, Preferably, the volatile non-silicone oils have a flash point of at least 40° C.

When present, the total amount of volatile oil may be present in the cosmetic composition in an amount ranging from about 10% to about 40%, such as from about 15% to about 30%, by weight, relative to the cosmetic composition. When present, the volatile solvent may be present in the cosmetic composition in an amount ranging from about 10% to about 30%, such as from about 15% to about 25%, by weight, relative to the cosmetic composition.

Non-volatile oils may also be present in the long-wear cosmetic composition. According to the disclosure, they include but are not limited to polar oils such as hydrocarbon-based oils of animal origin, for example perhydrosqualene; hydrocarbon-based plant oils such as liquid triglycerides of fatty acids and of glycerol, in which the fatty acids may have varied chain lengths, these chains being linear or branched, and saturated or unsaturated, which can be chosen, for example, from wheatgerm oil, sunflower oil, corn oil, soybean oil, marrow oil, grapeseed oil, blackcurrant seed oil, sesame oil, hazelnut oil, apricot oil, macadamia oil, castor oil, avocado oil, karite butter, sweet almond oil, cotton oil, alfalfa oil, poppy oil, pumpkin oil, evening primrose oil, millet oil, barley oil, quinoa oil, olive oil, rye oil, safflower oil, candlenut oil, passion flower oil, musk rose oil and caprylic/capric acid triglycerides such as those sold by the company Stearineries Dubois or those sold under the names Miglyol 810, 812 and 818 by the company Dynamit Nobel; natural or synthetic esters of formula $R^1COOR^2$, wherein $R^1$ is a higher fatty acid residue comprising 7 to 19 carbon atoms, and $R^2$ is a branched hydrocarbon-based chain comprising 3 to 20 carbon atoms, such as, for example, purcellin oil (cetostearyl octanoate), isopropyl myristate and alkyl or polyalkyl octanoates, decanoates or ricinoleates; synthetic ethers of formula $R^3COR^4$, wherein $R^3$ is a $C_3$ to $C_{19}$ alkyl radical, and $R^4$ is a $C_3$ to $C_{20}$ alkyl radical; fatty alcohols comprising at least 12 carbon atoms, such as octyldodecanol or oleyl alcohol; cyclic hydrocarbons such as (alkyl)cycloalkanes, wherein the alkyl chain is linear or branched, saturated or unsaturated and comprises 1 to 30 carbon atoms, such as cyclohexane or dioctyl-cyclohexane; aromatic hydrocarbons, for example, alkenes such as benzene, toluene, 2,4-dimethyl-3-cyclohexene, dipentene, p-cymene, naphthalene or anthracene, and esters such as isostearyl benzoate; primary, secondary or tertiary amines such as triethanolamine; and mixtures thereof.

Additional Film Formers

In various embodiments, the long-wear cosmetic compositions may further comprise one or more additional film formers.

Without intending to be limiting, film formers may be chosen from any film forming polymer or resin capable, by itself or in the presence of an auxiliary film-forming agent, of forming a film that adheres to a support and especially to the skin. Among the film-forming polymers that may be used, mention may be made of synthetic polymers, of free-radical type or of polycondensate type, polymers of natural origin and mixtures thereof, such as acrylic polymers, polyurethanes, polyesters, polyamides, polyureas, cellulose-based polymers, for instance nitrocellulose, and latex film forming polymers. For example, latex film forming polymers may be chosen from acrylate latex polymers, polyurethane latex polymers, and mixtures thereof. As still further examples of film forming polymers, latex film forming polymers may be chosen from at least one random styrene acrylate copolymer or derivative thereof, and at least one acrylate copolymer or derivative thereof, and mixtures thereof. Further, resinous plant extracts such as rosin and shellac, or derivatives thereof, epoxy ester resins, polyvinylpyrrolidone (PVP), polyvinylpyrrolidone/vinyl acetate copolymers and vinyl acetate/crotonic acid copolymers, and silicone resins may also be mentioned.

By way of example, suitable film forming polymers and resins include sulfopolyester resins, such as AQ sulfopolyester resins, for example AQ29D, AQ35S, AQ38D, AQ38S, AQ48S, and AQ55S (available from Eastman Chemicals), Vinex resins, such as Vinex 2034, Vinex 2144, and Vinex 2019 (available from Air Products), Dermacryl acrylic resins (available from National Starch), polyvinlypyrrolidinones (PVP) such as Luviskol K17, K30, and K90 (available from BASF), water soluble copolymers of PVP, including PVP/VA S-630 and W-735 and PVP/dimethylaminoethylmethacrylate, and Copolymers such as Copolymer 845 and Copolymer 937 available from ISP.

The film former may be present in the cosmetic composition in an amount ranging from about 1% to about 20%, such as from about 5% to about 15%, by weight, relative to the cosmetic composition.

The long wear cosmetic composition may further comprise any component traditionally used in compositions for making up the skin, including but not limited to surfactants, co-solvents (volatile and/or non-volatile), waxes, plasticizers, preservatives, fillers, active ingredients used to treat skin, and sunscreens. Of course, the skilled artisan will take care to choose components that do not, or do not substantially, negatively affect the skin-tightening properties of the film produced by the skin-tightening compositions of the systems and methods described herein.

Skin-Tightening Compositions

According to various embodiments, the skin-tightening compositions useful in the systems and methods described herein comprise at least one thermoplastic elastomer, at least one adhesive polymer, and at least one filler, which together form an association to form a skin-tightening film on the skin upon application. Additional optional components, such as solvents, silicone elastomers, humectants, and water, may also be included in the skin-tightening compositions according to embodiments of the disclosure.

Thermoplastic Elastomer

According to various embodiments, the at least one thermoplastic elastomer is chosen from amorphous hydrocarbon block copolymers of styrene and monomers of hydrocarbon containing 2 to 5 carbon atoms and comprising one or two ethylenic unsaturations, and having at least two glass transition temperatures ("$T_g$"). The block copolymers may be hydrocarbon-soluble or dispersible in the oily phase.

Non-limiting examples of unsaturated hydrocarbon monomers having 2 to 5 unsaturated carbon atoms include ethylene, propylene, butadiene, isoprene or pentadiene. In various exemplary and non-limiting embodiments, block copolymers may be chosen from those comprising at least one styrene block and at least one block comprising units selected from butadiene, ethylene, propylene, butylene, isoprene, or mixtures thereof. The hydrocarbon-based block copolymer may, for example, be an optionally hydrogenated copolymer comprising styrene blocks and ethylene blocks/$C_3$-$C_4$ alkylene or isoprene blocks.

The amorphous hydrocarbon block copolymers comprise at least one first block whose $T_g$ is below about 20° C., such as below about 0° C., below about –20° C., or below about –40° C. The $T_g$ of the first block can, for example, range from about –150° C. to about 20° C., such as from about –100° C. to about 0° C. The block copolymers also comprise at least one second block whose $T_g$ is greater than about 25° C., such as greater than about 50° C., greater than about 75° C., greater than about 100° C., or greater than about 150° C. The $T_g$ of the second block can, for example, range from about 25° C. to about 150° C., such as from about 50° C. to about 125° C., about 60° C. to about 120° C., or about 70° C. to about 100° C.

Exemplary, non-limiting amorphous diblock copolymers may be chosen from styrene-ethylene/propylene copolymers, styrene-ethylene/butadiene copolymers, styrene-ethylene/butylene copolymers, styrene-butadiene, or styrene-isoprene copolymers. Diblock copolymers are sold, for example, under the name Kraton® G1701E by Kraton Polymers.

Exemplary, non-limiting amorphous triblock amorphous copolymers may be chosen from styrene-ethylene/propylene-styrene copolymers, styrene-ethylene/butadiene-styrene copolymers, copolymers of styrene-isoprene-styrene, and copolymers of styrene-butadiene-styrene, such as those sold under the names Kraton® G1650, Kraton® D1101, D1102 Kraton®, Kraton® D1160 by Kraton Polymers. In one exemplary embodiment, the thermoplastic elastomer may be a mixture of a triblock copolymer styrene-butylene/ethylene-styrene diblock copolymer and a styrene-ethylene/butylene, such as those sold under the name Kraton® G1657M by Kraton Polymers.

The thermoplastic elastomer may be present in the skin-tightening composition in an amount up to about 25%, such as an amount ranging from about 5% to about 20%, about 6% to about 18%, about 7% to about 16%, about 8% to about 15%, about 9% to about 14%, by weight, relative to the weight of the composition.

Adhesive Polymer

Skin-tightening compositions according to the disclosure further comprise at least one adhesive film-forming polymer chosen from polymer particles of $C_1$-$C_4$ alkyl(methacrylate) polymer, stablilized in a non-aqueous dispersion, referred to herein for ease of reference as an "oil dispersion," such as those described in WO2015/091513 which is incorporated by reference herein.

By way of example, the $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth)acrylate and tert-butyl (meth)acrylate. For example, the polymer may be a methyl acrylate and/or ethyl acrylate polymer.

The polymer may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof. For example, the ethylenically unsaturated acid monomer may be chosen from (meth)acrylic acid, maleic acid, and maleic anhydride.

The salts may be chosen from salts of alkali metals, for example sodium or potassium; salts of alkaline-earth metals, for example calcium, magnesium or strontium; metal salts, for example zinc, aluminum, manganese or copper; ammonium salts of formula $NH^+$, quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles of the oil dispersion may thus comprise or consist essentially of about 80% to about 100%, by weight, of $C_1$-$C_4$ alkyl (meth)acrylate and of about 0% to about 20%, by weight, of ethylenically unsaturated acid monomer, relative to the total weight of the polymer. According to one exemplary embodiment, the polymer consists essentially of a polymer of one or more $C_1$-$C_4$ alkyl (meth)acrylate monomers. According to another exemplary embodiment, the polymer consists essentially of a copolymer of $C_1$-$C_4$ (meth)acrylate and of (meth)acrylic acid or maleic anhydride.

By way of non-limiting example only, the polymer of the particles in the oil dispersion, which may optionally be crosslinked or alternatively may not be crosslinked, may be chosen from methyl acrylate homopolymers, ethyl acrylate homopolymers, methyl acrylate/ethyl acrylate copolymers, methyl acrylate/ethyl acrylate/acrylic acid copolymers, methyl acrylate/ethyl acrylate/maleic anhydride copolymers, methyl acrylate/acrylic acid copolymers, ethyl acrylate/acrylic acid copolymers, methyl acrylate/maleic anhydride copolymers, and ethyl acrylate/maleic anhydride copolymers.

The polymer of the particles in the dispersion may have a number-average molecular weight ranging from about 2000 to about 10,000,000, for example ranging from about 150,000 to about 500,000. The polymer particles may be present in the oil dispersion in a content ranging from about 20% to about 60%, for example about 21% to about 58.5%, about 30% to about 50%, about 35% to about 45%, or about 36% to about 42%, by weight, relative to the total weight of the oil dispersion.

The stabilizer in the oil dispersion may be an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than about 4, for example greater than about 4.5, or greater than about 5. For example, the weight ratio may range from about 4.5 to about 19, such as from about 5 to about 19, or from about 5 to about 12.

By way of example only, the stabilizer may be chosen from isobornyl acrylate homopolymers, statistical copolymers of isobornyl acrylate/methyl acrylate, statistical copolymers of isobornyl acrylate/methyl acrylate/ethyl acrylate, and statistical copolymers of isobornyl methacrylate/methyl acrylate.

In various embodiments, the stabilizer may have a number-average molecular weight ranging from about 10,000 to about 400,000, such as from about 20,000 to about 200,000.

In various embodiments, the combination of the stabilizer+polymer of the particles present in the oil dispersion comprises from about 10% to about 50%, such as about 15% to about 30%, by weight of polymerized isobornyl (meth)acrylate, and from about 50% to about 90%, such as about 70% to about 85%, by weight of polymerized $C_1$-$C_4$ alkyl (meth)acrylate, relative to the total weight of the combination of the stabilizer+polymer of the particles.

The oily medium of the oil dispersion comprises a hydrocarbon-based oil. The hydrocarbon-based oil is an oil that is liquid at room temperature (25° C.). The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

Exemplary and non-limiting embodiments of the hydrocarbon-based oil medium of the oil dispersion include hydrocarbon-based oils containing up to about 40, such as from 8 to 16 or from 8 to 14, carbon atoms. Optionally, the hydrocarbon-based oil is apolar. For example, the hydrocarbon based oil may be chosen from isododecane.

The oil dispersion may be prepared, for example, as described in WO2015/091513.

In various embodiments, the adhesive polymer may have a $T_g$ greater than about 25° C., such as greater than about 50° C., greater than about 75° C., or greater than about 100° C., according to various embodiments.

The at least one adhesive polymer may be present in the skin-tightening composition in an amount up to about 25%, such as an amount ranging from about 5% to about 20%, about 6% to about 18%, about 7% to about 16%, about 8% to about 15%, about 9% to about 14%, or relative to the weight of the composition.

Fillers

The skin-tightening compositions may optionally comprise at least one filler. The fillers may be mineral or organic in nature, and of any shape. In various embodiments, the fillers may have a particle size greater than about 100 nm, and/or a specific surface area greater than about 200 m$^2$/g.

By way of non-limiting example, fillers may be chosen from talc, mica, silica, silica surface-treated with a hydrophobic agent, fumed silica, kaolin, polyamide (Nylon®) powders (e.g. Orgasol® from Atochem), polyurethane powders, poly-8-alanine powder and polyethylene powder, powders of tetrafluoroethylene polymers (Teflon®), lauroyllysine, starch, boron nitride, hollow polymer microspheres such as those of polyvinylidene chloride/acrylonitrile, for instance Expancel® (Nobel Industrie) or of acrylic acid copolymers (Polytrap® from the company Dow Corning) and silicone resin microbeads (Tospearls® from Toshiba, for example), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc stearate, magnesium stearate or lithium stearate, zinc laurate or magnesium myristate.

In at least certain embodiments, the at least one filler may be chosen from hydrophobic silica aerogel particles. Silica aerogels are porous materials obtained by replacing (by drying) the liquid component of a silica gel with air. Hydrophobic silica aerogel particles useful according to embodiments of the disclosure include silylated silica (INCI name: silica silylate) aerogel particles. The preparation of hydrophobic silica aerogel particles that have been surface-modified by silylation is described more fully in U.S. Pat. No. 7,470,725, incorporated by reference herein.

In various embodiments, aerogel particles of hydrophobic silica surface-modified with trimethylsilyl groups may be chosen. For example, the aerogel sold under the name VM-2260® by the company Dow Corning, the particles of which have an average size of about 1000 microns and a specific surface area per unit of mass ranging from 600 to 800 m$^2$/g, or the aerogel sold under the name VM-2270®, also by the company Dow Corning, the particles of which have an average size ranging from 5 to 15 microns and a specific surface area per unit of mass ranging from 600 to 800 m$^2$/g, may be chosen. In other embodiments, the aerogels sold by the company Cabot under the names Aerogel TLD 201®, Aerogel OGD 201®, and Aerogel TLD 203®, CAB-O-SIL TS-530, CAB-O-SIL TS-610, CAB-O-SIL TS-720, Enova Aerogel MT 1100®, and Enova Aerogel MT 1200®, may be chosen.

Optionally, mixtures of fillers may be present in the skin-tightening compositions according to the disclosure. For example, a mixture of different aerogel particles, or of an aerogel and a different type of filler, may be used.

The at least one filler may be present in a total amount ranging from about 0.1% to about 20% by weight, for example from about 0.2% to about 15%, from about 0.5% to about 10%, or from about 1% to about 6%, by weight, relative to the total weight of the skin-tightening composition. In at least certain exemplary embodiments, the filler is present in an amount less than about 5%, such as less than about 4%, by weight, relative to the total weight of the skin-tightening composition. In one embodiment, the filler is present in an amount up to about 3% by weight, relative to the total weight of the skin-tightening composition.

Additional Components

The skin-tightening compositions according to the disclosure may optionally further comprise additional components, such as solvents, silicone elastomers, humectants, water, and pigments.

Solvents

The skin-tightening compositions may comprise at least one solvent. Optionally, the skin-tightening compositions may comprise at least one solvent chosen from solvents having a vapor pressure at room temperature (25° C.) of greater than about 100 Pa, such as greater than about 500 Pa, or greater than about 1000 Pa. In various embodiments, the composition is free or substantially free of solvents having a vapor pressure at room temperature (25° C.) of less than about 25 Pa. In further embodiments, the skin-tightening composition may comprise at least one solvent having a vapor pressure at room temperature (25° C.) of greater than about 100 Pa, such as greater than 500 Pa, or greater than 1000 Pa, and at least one solvent having a vapor pressure at room temperature (25° C.) of less than about 100 Pa, such as less than about 50 Pa, or less than about 25 Pa.

In various embodiments, the skin-tightening compositions comprise at least one volatile organic solvent. The volatile organic solvent may be chosen from, for example, volatile hydrocarbon-based oils and volatile silicone oils.

For example, volatile hydrocarbon oils include, but are not limited to, those having from 8 to 16 carbon atoms and their mixtures, such as branched $C_8$ to $C_{16}$ alkanes and $C_8$ to $C_{16}$ isoalkanes (also known as isoparaffins), isododecane, isodecane, isohexadecane. For example, the at least one solvent may be chosen from the oils sold under the trade names of Isopar® or Permethyl®, the $C_8$ to $C_{16}$ branched esters such as isohexyl or isodecyl neopentanoate and their mixtures. In at least certain embodiments, the volatile hydrocarbon oils have a flash point of at least 40° C. It is also possible to use mixtures of isoparaffins and other volatile hydrocarbon-based oils, such as petroleum distillates.

Further, volatile silicone oils may be chosen from linear or cyclic silicone oils, such as those having a viscosity at room temperature (25° C.) of less than or equal to 6 cSt and having from 2 to 7 silicon atoms, these silicones being optionally substituted with alkyl or alkoxy groups of 1 to 10 carbon atoms. Examples of volatile silicone oils that may be used include, but are not limited to, octamethyltetrasiloxane, decamethylcyclo-pentasiloxane, dodecamethylcyclohexasiloxane, heptamethyloctyltrisiloxane, hexamethyldisiloxane, decamethyltetrasiloxane, dodecamethylpentasiloxane, and their mixtures. In at least certain embodiments, the volatile silicone oils have a flash point of at least 40° C.

Additionally, the at least one volatile solvent may be chosen from polar volatile solvents, including but not limited to, alcohols, volatile esters and volatile ethers.

The at least one solvent may be present in the skin-tightening composition in an amount up to about 95%, such as up to about 90%, up to about 85%, up to about 80%, up to about 75%, up to about 70%, up to about 65%, up to about 60%, up to about 55%, or up to about 50%, by weight of the composition. For example, the at least one solvent may be present in the skin-tightening composition in an amount ranging from about 40% to about 95%, such as about 50% to about 90%, or about 60% to about 85%, or about 65% to about 80%, by weight of the composition.

Silicone Elastomer

The skin-tightening composition may further optionally comprise at least one silicone elastomer. Surprisingly, in certain embodiments, the at least one silicone elastomer may improve properties such as the thickness and water-resistance of the skin-tightening film, without significantly affecting the mechanical or optical properties of the film. In other embodiments, the addition of at least one silicone elastomer may decrease wettability by sebum, which will help prevent the film from losing tightening properties. It may, in at least certain embodiments, be advantageous to choose a silicone elastomer having greater than 1% active material (AM), such as greater than 2% AM.

The at least one silicone elastomer may, for example, be chosen from at least one silicone crosspolymer dispersed in at least one oil. The at least one silicone crosspolymer may, in certain embodiments, be chosen from dimethicone crosspolymers, such as dimethicone/vinyl dimethicone crosspolymers and dimethicone/phenyl vinyl dimethicone crosspolymers. In other embodiments, the silicone crosspolymer may be modified by one or more groups chosen from alkyl, polyether, polyglycerin groups. For instance, the alkyl modified silicone cross-polymers may be chosen from vinyl dimethicone/lauryl dimethicone cross-polymers, cetearyl dimethicone cross-polymers, and $C_{30}$-$C_{45}$ alkyl cetearyl dimethicone cross-polymers. Non-limiting examples of polyether modified silicone cross-polymers include dimethicone/PEG-10/15 cross-polymers. Exemplary alkyl and polyether modified silicone cross-polymers may be chosen, for example, from PEG-10/lauryl dimethicone cross-polymers and PEG-15/lauryl dimethicone cross-polymers. Exemplary polyglycerin modified silicone cross-polymers include dimethicone/polyglycerin-3 cross-polymers and lauryl dimethicone/polyglycerin-3 cross-polymers.

In at least certain embodiments, the silicone polymers do not comprise polyethylene glycol or polypropylene groups, or hydrophilic moieties. Optionally, the silicone elastomer may be chosen from the silicone organic blends isododecane (and) dimethicone crosspolymer (18% AM) sold under the name EL-8040 ID or dimethicone/bis-isobutyl PPG-20 crosspolymer (17% AM in isododecane) sold under the name EL-8050 ID, by Dow Corning; or isododecane (and) vinyldimethyl/trimethylsiloxysilicate stearyl dimethicone crosspolymer (20% AM in isododecane), sold under the name GEL BELSIL RG90 by Wacker.

The silicone crosspolymer may be dispersed in at least one oil. In certain embodiments, the oil may be chosen from silicone oils, such as cyclic and linear organopolysiloxanes. Cyclic organopolysiloxanes may include, for example, cyclotetrasiloxane; cyclopentasiloxane; and methylated cyclic organopolysiloxanes, for example, octamethylcyclotetrasiloxane and decamethylcyclopentasiloxane. Non-limiting examples of linear organopolysiloxanes include low molecular weight dimethicones; high molecular weight dimethicones; alkyl derivatives of linear organopolysiloxanes, for example, cetyl dimethicone and lauryl trimethicone; aryl derivatives of linear organopolysiloxanes, for example, phenyl trimethicone; and hydroxylated derivatives of linear organopolysiloxanes, for example, dimethiconol. In other embodiments, the oil may be chosen from organic oils, such as mineral oil; linear and branched alkanes, for example, isododecane; triethylhexanoin; and squalane.

The at least one silicone crosspolymer may, in some embodiments, comprise from about 5% to about 35% by weight, relative to the total weight of the silicone elastomer blend, for example, from about 10% to about 20% by weight, or from about 25% to about 35% by weight, or from about 20% to about 30% by weight. The at least one oil may comprise from about 65% to about 95% by weight, relative to the total weight of the silicone elastomer blend, such as from about 80% to about 90% by weight, or from about 65% to about 75% by weight, or from about 70% to about 80% by weight.

In various exemplary embodiments, the silicone elastomer blend comprises from about 20% to about 30% of dimethicone/vinyl dimethicone cross-polymer. In further exemplary embodiments, the silicone elastomer blend comprises from about 70% to about 80% by weight of dimethicone. In yet further exemplary embodiments, the silicone elastomer blend comprises from about 20% to about 30% of dimethicone/vinyl dimethicone cross-polymer and from about 70% to about 80% by weight dimethicone.

For example, silicone elastomers sold under the name KSG-16 dimethicone (and) dimethicone/vinyl dimethicone corpsspolymer, KSG-21 (at 27% in active material) INCI name: Dimethicone/PEG-10 Dimethicone vinyl dimethicone crosspolymer), KSG-20 (at 95% % in active material) INCI name: PEG-10 Dimethicone Crosspolymer), KSG-30, (at 100% % in active material) INCI name: Lauryl PEG-15 Dimethicone vinyl dimethicone crosspolymer), KSG-31 (at 25% in active material) INCI name: Lauryl PEG-15 Dimethicone vinyl dimethicone crosspolymer), KSG-32 or KSG-42 or KSG-320 or KSG-30 (at 25% in active material) INCI name: Lauryl PEG-15 Dimethicone vinyl dimethicone crosspolymer), KSG-33: Lauryl PEG-15 (at 20% in active material) Dimethicone vinyl dimethicone crosspolymer), KSG-210 (at 25% in active material) INCI name: Dimethicone/PEG-10/15 crosspolymer), KSG-310: lauryl modified polydimethylsiloxane polyoxyethylenated in mineral oil, KSG-330 and KSG-340: PEG-15/lauryl dimethicone crosspolymer, and X-226146 (at 32% % in active material) INCI name: Dimethicone/PEG-10 Dimethicone vinyl dimethicone crosspolymer), all by Shin Etsu; DC9010 (at 9% in active material) and DC9011 (at 11% in active material) INCI name: PEG-12 dimethicone crosspolymer), DC9040 cyclopentasiloxane (and) dimethicone crosspolymer, and DC9041 dimethicone (and) dimethicone crosspolymer, all by Dow Corning; or the products sold under the VELVESIL product line by Momentive, such as VELVESIL 125 and VELVESIL DM, may be chosen.

Other examples of silicone elastomers include KSG-710 (at 25% in active material, INCI name: dimethicone/polyglycerin-3 crosspolymer); and KSG-820, KSG-830 and KSG-840, all of which are dimethicone/polvaleverin-3 crosspolymer (INCI), but in different diluents, 820 is in isododecane, 830 is in triethyl hexanoin, and 840 is in squalene, all by Shin Estu.

The at least one silicone elastomer may optionally be included in the skin-tightening composition in an amount up to about 10%, such as up to about 8%, up to about 5%, about 4.5%, up to about 4%, up to about 3.5%, up to about 3%, up to about 2.5%, up to about 2%, up to about 1.5%, up to about 1%, up to about 0.75%, up to about 0.5%, up to about 0.25%, up to about 0.2%, or up to about 0.1%, by weight, relative to the weight of the composition. In certain embodiments, the at least one silicone elastomer may be present in an amount ranging from about 1% to about 10%, such as about 2% to about 8%, about 3% to about 6%, or about 4% to about 5%, by weight, relative to the weight of the skin-tightening composition.

Humectants

Optionally, skin-tightening compositions according to the disclosure may comprise at least one humectant or moisturizing agent. Surprisingly, in at least certain embodiments, the at least one humectant may improve the optical properties and feeling of the film formed on the skin by the composition, without negatively affecting the skin-tightening properties of the film.

By way of example only, humectants or moisturizing agents may be chosen from polyhydroxy compounds including but not limited to glycerin and glycols such as, for example, propylene glycol, butylene glycol, dipropylene glycol and diethylene glycol, glycol ethers such as monopropylene, dipropylene and tripropylene glycol alkyl($C_1$-$C_4$) ethers, monoethylene, diethylene and triethylene glycol.

The at least one humectant may be present in the skin-tightening composition in an amount up to about 20%, such as up to about 15%, up to about 14%, up to about 13%, up to about 12%, up to about 11%, up to about 10%, up to about 9%, up to about 8%, up to about 7%, up to about 6%, up to about 5%, up to about 4%, up to about 3%, up to about 2%, up to about 1%, or up to about 0.5%, by weight of the composition.

Water

Optionally, in at least certain embodiments, water may be added to the skin-tightening compositions according to the disclosure. Surprisingly, in certain non-limiting embodiments, water may improve the properties of the film formed on the skin by the composition, such as Young Modulus, transparency, cohesion, and thickness.

Water can be included in the skin-tightening composition in an amount up to about 15%, up to about 12%, up to about 10%, up to about 9%, up to about 8%, up to about 7%, up to about 6%, up to about 5%, up to about 4%, up to about 3%, up to about 2%, up to about 1%, or up to about 0.5%, by weight of the composition. In at least certain embodiments, the skin-tightening compositions are anhydrous or substantially anhydrous. In other embodiments, the skin-tightening compositions may be in the form of a water-in-oil (W/O) emulsion.

It may, in at least certain embodiments, be advantageous to include water and at least one humectant, for example water and glycerin, in the skin-tightening composition together.

Skin-Tightening Film

When the skin-tightening compositions according to the disclosure are applied to the skin, the at least one thermoplastic elastomer, the at least one adhesive polymer, and the at least one filler together form a matrix that creates a film on the skin. The film formed by the compositions described herein form quickly, are long-lasting and durable, and have optical properties that are advantageous for a skin-tightening film, such as transparency, matte effect, and a soft focus effect which helps to blur skin imperfections so that they are less noticeable.

Additionally, as discussed above, the compositions according to the disclosure form a film that is stiffer than, and thus capable of tightening, human skin. Human skin has a Young Modulus in the range of 10 kPa to 100 kPa; thus, a film for tightening the skin should have a Young Modulus of greater than 100 kPa. The films that are formed by the compositions have Young Modulus' greater than 500 kPa (0.5 MPa) in some embodiments, greater than 1000 kPa (1 MPa) in some embodiments, greater than 5000 kPa (5 MPa) in some embodiments, and even greater than 10,000 kPa (10 MPa) in some embodiments. Additionally, the compositions according to the disclosure have sufficient consistency G* and phase angle below 45°, in order to form an effective and lasting film on the skin.

As such, the amounts and components of the composition should be chosen to provide a film on the skin that is capable of tightening the skin, while also blurring skin imperfections.

In various exemplary embodiments, for the best film properties, it may be advantageous for the total amount of thermoplastic elastomer plus adhesive polymer plus filler to be greater than about 10%, such as greater than about 15% or greater than about 20%, by weight, of the total weight of the composition.

In yet further exemplary embodiments, for the best film properties, it may be advantageous for amounts of the thermoplastic elastomer and adhesive polymer to be chosen so that the ratio of thermoplastic elastomer:adhesive polymer is in the range of about 1:10 to 10:1, in the range of about 1:5 to 5:1, or in the range of about 1:1 to 8:1.

The films may be formed quickly, for example within less than about 30 minutes, less than about 20 minutes, less than about 10 minutes, or less than about 5 minutes, after the composition is applied to the skin.

Films according to the disclosure may be long-lasting. For example, once the composition is applied to the skin and a film is formed, the film may remain substantially intact on the skin for a period of at least about 12 hours, such as at least about 24 hours, at least about 48 hours, or at least about 72 hours.

The films may also be durable. For example, the film may not rub off, may not come off with sweat, or when the film is contacted by water, makeup, lotions, or other products that the user may wish to put on the skin.

Methods

Methods of improving the appearance of the skin using the systems described herein are also disclosed, said methods comprising applying a skin-tightening composition according to the disclosure onto the skin in order to form a film on the skin, either before or after applying a long-wear cosmetic composition to the skin. Methods comprise tightening the skin, e.g. to get rid of, or reduce the appearance of, wrinkles, eye bags, etc., while also blurring or hiding skin imperfections, e.g. to camouflage pimples, pores, dark spots, uneven pigmentation, etc.

Optionally, in various methods, the skin tightening composition of the systems described herein may be applied to the skin first as a base coat, followed by an optional drying time during which a skin-tightening film is formed on the skin, followed by applying the long-wear cosmetic composition onto the skin on top of the film.

In further methods, the long-wear cosmetic composition of the systems described herein may be applied to the skin first as a base coat, followed by an optional drying time to allow the cosmetic composition to dry, and followed by applying the skin-tightening composition onto the skin on top of the cosmetic composition to form a skin-tightening film thereon.

Surprisingly and unexpectedly, the skin-tightening composition works in synergy with the long-wear cosmetic composition. The systems and methods described herein avoid or minimize the drawback of migration of pigments from the long-wear cosmetic composition. Furthermore, the association of the skin-tightening composition and the long-wear cosmetic composition avoids or minimizes the softening of the skin-tightening film, which can diminish the film's skin-tightening properties.

Further, the systems and methods described herein provides for an appearance of the skin that has a substantially homogenous coloration that is long-lasting and durable. The systems and methods thus effectively hide skin imperfections while simultaneously minimizing the appearance of wrinkles. In at least certain embodiments, the appearance of skin imperfections, wrinkles, or both may be minimized to a greater extent with the systems and methods of the disclosure, as compared to either skin-tightening compositions or long-wear cosmetic compositions alone.

Kits

The disclosure further relates to kits comprising, in one compartment, (1) a skin-tightening composition comprising (a) at least one amorphous hydrocarbon block copolymer of styrene and monomers of hydrocarbon containing 2 to 5 carbon atoms and comprising one or two ethylenic unsaturations, and having a first $T_g$ below about 0° C., and a second $T_g$ greater than about 25° C., (b) at least one adhesive film-forming polymer chosen from polymer particles of $C_1$-$C_4$ alkyl(methacrylate)polymer, stablilized in a non-aqueous dispersion, and (c) at least one filler; and in a second compartment (2) a long-wear cosmetic composition comprising at least one silicone-polyamide copolymer, at least one silicone film former, and at least one volatile oil.

It to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints.

It is understood that when an amount of a component is given, it is intended to signify the amount of the active material.

It should be understood that all patents and published patent applications referenced are incorporated herein in their entireties.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

The compositions and methods according to the present disclosure can comprise, consist of, or consist essentially of the elements and limitations described herein, as well as any additional or optional ingredients, components, or limitations described herein or otherwise known in the art.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

EXAMPLES

The following Examples are provided for illustrative purposes only, and are not intended to be limiting.

In each of the following examples, the amounts of components given are in terms of active material (AM).

Dynamic Mechanical Analysis (DMA)

The determination of Young Modulus of the films for all Examples was as follows. The film was made by using a draw down bar at 8" to cast the solution on a Teflon plate and dried the film at 40° C. in an oven overnight. The DMA Q800FR from TA instruments was used to measure the stress-strain response of the dried film. The deformation was applied from 0% strain to 200% strain at a rate of 100% strain/min at 32° C. Then the Young Modulus of the film was determined from the slope of the stress-strain curve in the linear viscoelastic regime.

Example 1

Skin-Tightening Composition

A skin-tightening composition according to the disclosure was prepared as follows. The thermoplastic elastomer, Kraton (25%), was dispersed in isoparaffin oil with a mechanical stirrer and heated to 90° C. Stirring continued at 90° C. for 1-2 hours until all Kraton polymer was dissolved and the polymer solution became clear. The desired amounts of adhesive polymer and silica silylate were added into the Kraton/isoparaffin oil solution at the specified ratios in a plastic container, and the solution was mixed with a high speed mixer at 2500 rpm/min for 5 minutes. The final solution was kept at room temperature and sealed to avoid the evaporation of solvents.

Table 1 shows the skin-tightening composition prepared according to the disclosure:

TABLE 1

| Skin-tightening Composition | |
|---|---|
| Component | Amount (%) |
| HYDROGENATED STYRENE/BUTADIENE COPOLYMER | 11.1 |
| OIL DISPERSION | 11.1 |
| ISODODECANE (AND) DIMETHICONE CROSSPOLYMER | 4.5 |

TABLE 1-continued

Skin-tightening Composition

| Component | Amount (%) |
|---|---|
| SILICA SILYLATE | 3.0 |
| C8-9 ISOPARAFFIN | 33.3 |
| ISODODECANE | 37.0 |
| Total | 100.0% |
| Young Modulus (37° C.) | 24 MPa |

The Young Modulus of the film formed from the skin-tightening composition in Table 1 is 24 MPa at 37° C., which is greater than the Young Modulus of skin. Thus, the skin-tightening composition is able to produce a film capable of tightening the skin to minimize the appearance of wrinkles, crow's feet, eye bags, etc.

Example 2

Long-Wear Cosmetic Compositions

Tables 2-5 illustrate examples of long-wear cosmetic compositions.

TABLE 2

Long-Wear Foundation Composition

| Phase | INCI Name | Amount (%) |
|---|---|---|
| A | Cyclopentasiloxane (and) dimethicone copolyol | 8.0 |
|   | Polyglyceryl-4 isostearate (and) hexyl laurate (and) cetyl PEG/PPG-10/1 dimethicone | 3.5 |
|   | Treated pigments | 9.9 |
| B1 | Cyclopentasiloxane (volatile oil) | 26.1 |
|   | Polysiloxane/polyamide (PASi) | 3.0 |
| B2 | Polytrap/cyclopentasiloxane (filler) | 1.0 |
|   | MMA crosspolymer (filler) | 4.0 |
|   | Nylon-12 (filler) | 1.0 |
| B3 | Preservative | 0.4 |
|   | Disteardimonium Hectorite | 0.6 |
|   | Propylene carbonate | 0.2 |
| C | Water | 40.0 |
|   | Magnesium sulfate | 1.0 |
|   | Preservatives | 0.7 |
|   | Non-ionic emulsifier | 0.5 |
| Total | | 100.0% |

The foundation is obtained by heating phase B1 until softening of this phase; adding phase B2 with stirring, then phase B3; adding phase A at a temperature 20° C. below the preceding temperature, then adding phase C under stirring.

The product obtained in this way has, because of the incorporation into the liquid fatty phase of a polysiloxane (PS) polyamide (PA) polymer, according to the invention, excellent non-transfer properties (demonstrated by the non-deposition of foundation on a small collar placed around the neck of made-up testers for several minutes).

TABLE 3

Long-Wear Foundation Composition

| Phase | INCI Name | Amount (%) |
|---|---|---|
| A | Cyclopentasiloxane (and) dimethicone copolyol | 8.0 |
|   | Polyglyceryl-4 isostearate (and) hexyl laurate (and) cetyl (PEG/PPG-10/1 dimethicone | 3.5 |
|   | Pigments | 9.9 |
| B1 | Cyclopentasiloxane | 16.1 |
|   | Polysiloxane/polyamide PASi (MW: $14 \times 10^4$, DP 15) | 1.0 |
|   | Silicone-acrylates | 12.0 |
| B2 | Polytrap/cyclopentasiloxane (filler) | 1.0 |
|   | MMA Crosspolymer (filler) | 4.0 |
|   | Nylon-12 (filler) | 1.0 |
| B3 | Preservatives | 0.4 |
|   | Disteardimonium Hectorite (gelling agent) | 0.6 |
|   | Propylene Carbonate | 0.2 |
| C | Water | 40.0 |
|   | Magnesium sulfate | 1.0 |
|   | Methylparaben (preservative) | 0.7 |
|   | Non-ionic emulsifier | 0.5 |
| Total | | 100.0% |

This foundation is obtained in the following manner: heating of the silicone polyamide in the non-volatile oils until obtaining of a liquid mixture, addition of pigments, fillers, gelling agent, surfactants, then volatiles at 20° C. below the softening point of the polymer, addition of the aqueous phase, preservatives, and magnesium sulfate, then homogenization of the whole. The product obtained then is poured into a suitable container, of the foundation-case type.

The product obtained in this manner has, because of the incorporation into the liquid fatty phase of the combination of a polysiloxane (PS)/polyamide (PA) polymer and silicone acrylates, excellent non-transfer properties (demonstrated by the non-deposition of foundation on a small collar placed around the neck of made-up testers for several minutes). In addition, this foundation has the following properties: non-stickiness, flexibility, comfort, freshness. It makes possible a good application ("good application with cushion") and the deposit has an excellent resistance to water.

TABLE 4

Long-Wear Foundation Composition

| Phase | INCI Name | Amount (%) |
|---|---|---|
| A | Ethylhexyl Methoxycinnamate | 4.0 |
|   | Cyclopentasiloxane (and) dimethicone copolyol | 8.0 |
|   | Cyclopentasiloxane (and) diphenyl dimethicone | 2.0 |
|   | Pigments | 9.9 |
| B | Cyclopentasiloxane | 18.0 |
|   | Polysiloxane/polyamide | 3.0 |
|   | Polyglyceryl-4-isostearate (and) hexyl laurate (and) cetyl PEG/PPG-10/1 dimethicone | 3.5 |
|   | Preservative | 0.2 |
| C | MMA crosspolymer (filler) | 4.5 |
|   | Polytrap in cyclopentasiloxane (filler) | 0.9 |
|   | Silica (filler) | 0.64 |
| D | Water | 32.16 |
|   | Butylene glycol (moisturizer) | 10.0 |
|   | Magnesium sulfate | 1.0 |
|   | Methylparaben (preservative) | 0.3 |
|   | Non-ionic emulsifier | 0.5 |
| E | Water | 1.0 |
|   | Preservative | 0.3 |
| Total | | 100.00% |

The foundation of Table 4 is obtained in the following manner: phase A is prepared by mixing the ingredients well and grinding them with a SILVERSON homogenizer at a speed of 6000 rpm. Separately, the phase B ingredients are heated to 80 to 85° C., with stirring for 10 to 15 minutes, or until dissolution of the polysiloxane/polyamide. Phases A and B then are combined in the main beaker and mixed well at the temperature of 60 to 65° C. Phase C is added to the main beaker and it is stirred until obtaining of a uniform mixture.

Phase D is heated to 65 to 70° C. in a separate side beaker. Emulsification is carried out by adding phase D to the main beaker with the aid of a homogenizer at medium/high speed. The product is cooled to 40 to 45° C., then phase E is added slowly with thorough stirring. The product is cooled to room temperature, by means of a paddle stirrer.

TABLE 5

Long-Wear Foundation Composition

| Phase | INCI Name | Amount (%) |
|---|---|---|
| A | Ethylhexyl Methoxycinnamate | 4.0 |
|   | Cyclopentasiloxane (and) dimethicone copolyol | 8.0 |
|   | Cyclopentasiloxane (and) diphenyl dimethicone | 2.0 |
|   | Pigments | 9.9 |
| B | Cyclopentasiloxane | 18.0 |
|   | Polysiloxane/polyamide | 3.0 |
|   | Polyglyceryl-4-isostearate (and) hexyl laurate (and) cetyl PEG/PPG-10/1 dimethicone | 3.5 |
|   | Propylparaben | 0.2 |
| C | MMA crosspolymer | 4.5 |
|   | Polytrap/cyclopentasiloxane | 0.9 |
|   | Silica | 0.64 |
| D | Water | 42.16 |
|   | Magnesium sulfate | 1.0 |
|   | Preservative | 0.3 |
|   | Non-ionic emulsifier | 0.5 |
| E | Water | 1.0 |
|   | Preservative | 0.3 |
| Total |  | 100.00% |

The foundation is obtained in a manner comparable to that described previously for Table 4.

The product obtained in this manner has, because of the incorporation into the fatty phase of a polysiloxane/polyamide polymer, excellent cosmetic properties, in particular of non-transfer and staying power, and properties of "comfortable wear, "nice application with cushion" and it is light during application—"feel light during application."

The product obtained in this manner has, because of the incorporation into the liquid phase of a polysiloxane/polyamide polymer (PASi), excellent cosmetic properties, in particular an easy, flowing application ("nice application with cushion"), a good resistance to transfer after drying, a very good resistance to water, a high level of comfort ("comfortable wear").

Example 3

Methods for Improving the Appearance of the Skin

A long-wear composition was prepared as in Table 4, to evaluate the compatability with the skin-tightening composition for improving the appearance of the skin.

TABLE 6

Long-Wear Foundation Composition

| Phase | INCI Name | Amount |
|---|---|---|
| ACTIVE | MAGNESIUM SULFATE | 0.7 |
| CHARGE | SILICA | 1 |
| CHARGE | PERLITE | 0.2 |

TABLE 6-continued

Long-Wear Foundation Composition

| Phase | INCI Name | Amount |
|---|---|---|
| COLORANT | TITANIUM DIOXIDE (and) DISODIUM STEAROYL GLUTAMATE (and) ALUMINUM HYDROXIDE | 10.85 |
| COLORANT | IRON OXIDES (and) DISODIUM STEAROYL GLUTAMATE (and) ALUMINUM HYDROXIDE | 0.26 |
| COLORANT | IRON OXIDES (and) DISODIUM STEAROYL GLUTAMATE (and) ALUMINUM HYDROXIDE | 0.07 |
| COLORANT | IRON OXIDES (and) DISODIUM STEAROYL GLUTAMATE (and) ALUMINUM HYDROXIDE | 0.83 |
| CORPS GRAS | ISOHEXADECANE | 1.6 |
| FILTRE SOLAIRE | ETHYLHEXYL METHOXYCINNAMATE | 3 |
| POLYMERE | NYLON-12 | 3 |
| SILICONE | CYCLOHEXASILOXANE | 15.7 |
| SILICONE | CETYL PEG/PPG-10/1 DIMETHICONE | 1 |
| SILICONE | PEG-10 DIMETHICONE | 2 |
| SILICONE | ACRYLATES/POLYTRIMETHYL-SILOXYMETHACRYLATE COPOLYMER | 10 |
| SOLVENT | BUTYLENE GLYCOL | 6 |
| SOLVENT | ALCOHOL (DENATURED) | 8 |
| SOLVENT | WATER | 34.79 |
| SOLVENT | ISODODECANE | 1 |
| Total |  | 100.00% |

To improve the appearance of skin of a subject, the skin-tightening composition of Table 1 can be used as follows:

(i) with the skin-tightening composition applied as a base coat and allowed to dry, wherein a skin-tightening film was formed on the skin. A long-wear cosmetic composition may be subsequently applied on top of the film; and/or (ii) with a long-wear cosmetic composition applied to the skin as a base coat, followed by an optional drying period, and the skin-tightening composition applied on top so that a skin-tightening film formed on top of the long-wear cosmetic composition.

Example 4

Compatibility Between Skin-Tightening Composition and Long Wear Foundation

Test Objective: this study aimed to assess the efficacy of skin-tightening compositions over long wear foundations. The objective was to confirm skin-tightening composition usage with long wear foundation (expert application in controlled condition).

Application Method: Expert application in a controlled environment. Half face application skin-tightening composition only versus skin-tightening composition over foundation. Ratings and images were taken at baseline, 10 minutes, 30 minutes, 3 hours, 6 hours, and after removal. Expert applied a moisturizer, then applied the long wear foundation as described in Table 6 over half face, then applied a skin-tightening composition to the under-eye area and crow's feet on both sides. Application of the skin-tightening composition was performed using finger application.

Test Design: grade 4 Atlas score for under-eye bags; crow's feet and wrinkles under eyes were different grades (evaluations and photos at application, 10 minutes, 30 minutes, 3 hours, 6 hours, and removal). This was in a controlled environment.

Figure 2:
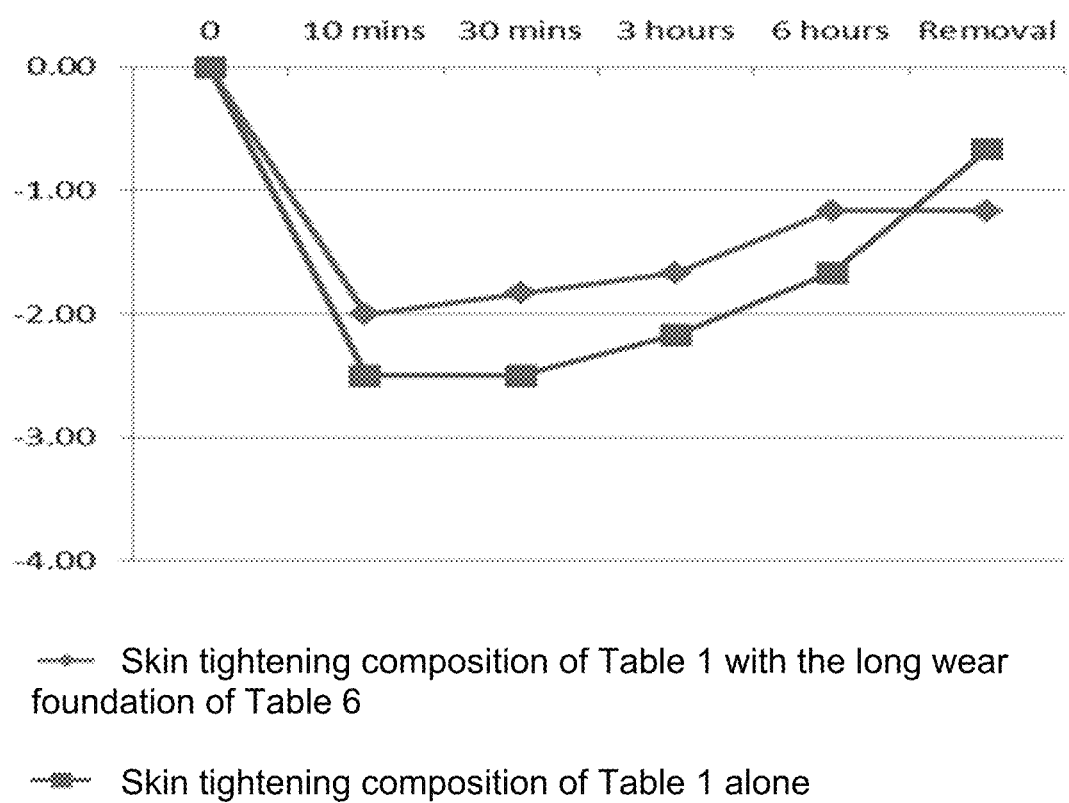
FIG. 2 demonstrates compatibility between an exemplary skin-tightening composition according to an embodiment of the disclosure and long wear foundation, and effect on under-eye crow's feet.
Figure 3:
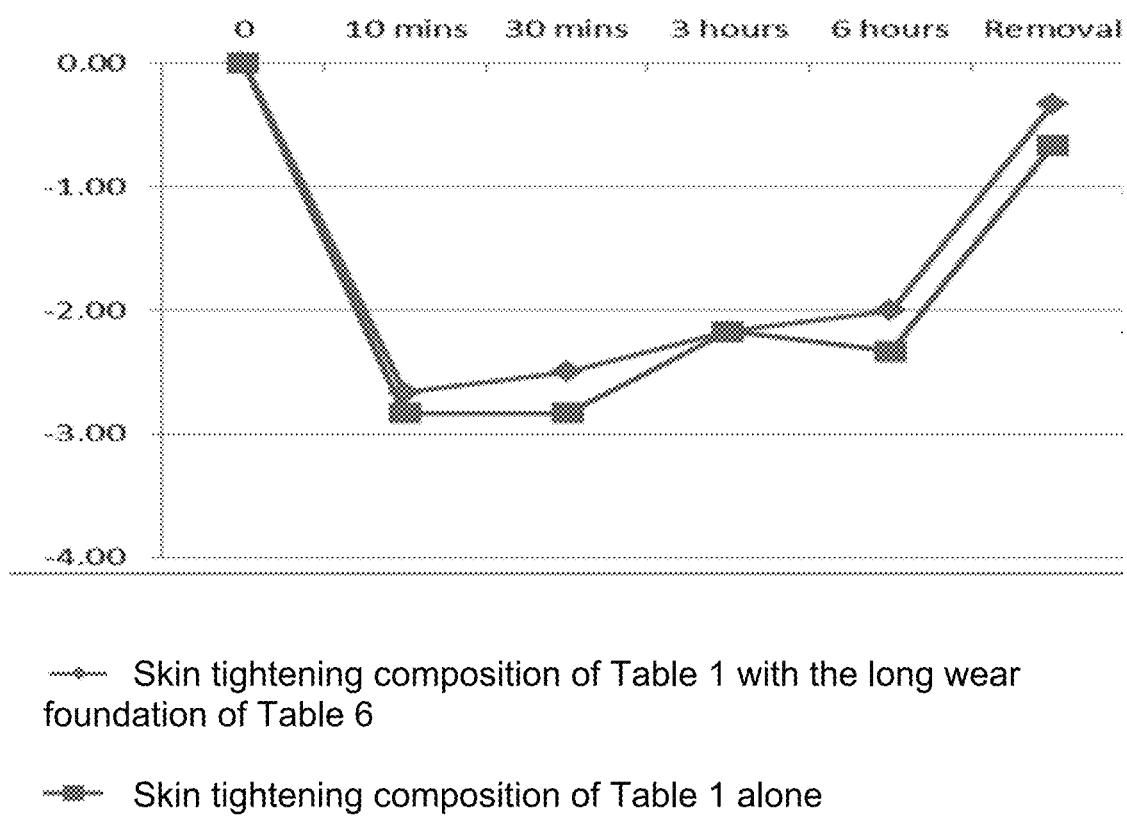
FIG. 3 demonstrates compatibility between an exemplary skin-tightening composition according to an embodiment of the disclosure and long wear foundation, and effect on under-eye wrinkles.

FIG. 1 shows results of evaluation of skin-tightening composition and compatibility with long wear foundation and effect on under-eye bag. FIG. 2 shows results of evaluation of skin-tightening composition and compatibility with long wear foundation and effect on crow's feet. FIG. 3 shows results of evaluation of skin-tightening composition and compatibility with long wear foundation and effect on under eye wrinkles. The results illustrate good compatibility of skin-tightening composition with long wear foundation. The results also demonstrate long lasting performance of the skin-tightening composition when used over foundation, and the long wear foundation also showed good performance in terms of cracking, pigment migration, demarcation, and appropriate coverage. Visual improvement in terms of effect on under-eye bags, crow's feet, and under-eye wrinkles is also noted in FIGS. 1-3.

We claim:

1. A method for improving the appearance of skin, said method comprising:
   (1) applying to the skin of a subject a long-wear cosmetic composition comprising at least one silicone-polyamide copolymer, at least one silicone film former, and at least one volatile oil;
   and, after an optional drying time;
   (2) forming a film on top of the long-wear cosmetic composition by applying a skin-tightening composition to the skin, the skin-tightening composition comprising:
      a. at least one thermoplastic elastomer chosen from amorphous hydrocarbon block copolymers of styrene and monomers of hydrocarbon containing 2 to 5 carbon atoms and comprising one or two ethylenic unsaturations, and having a first $T_g$ below about 0° C., and a second $T_g$ greater than about 25° C.;
      b. at least one adhesive film-forming polymer chosen from polymer particles of $C_1$-$C_4$ alkyl(methacrylate) polymer, stabilized in a non-aqueous dispersion; and
      c. at least one filler;
   wherein the Young Modulus of the film formed on the skin is greater than about 500 kPa.

2. A method for improving the appearance of skin, said method comprising:
   (1) forming a film on the skin by applying a skin-tightening composition to the skin, the skin-tightening composition comprising:
      a. at least one thermoplastic elastomer chosen from amorphous hydrocarbon block copolymers of styrene and monomers of hydrocarbon containing 2 to 5 carbon atoms and comprising one or two ethylenic unsaturations, and having a first $T_g$ below about 0° C., and a second $T_g$ greater than about 25° C.;
      b. at least one adhesive film-forming polymer chosen from polymer particles of $C_1$-$C_4$ alkyl(methacrylate) polymer, stabilized in a non-aqueous dispersion; and
      c. at least one filler,
   wherein the Young Modulus of the film formed on the skin is greater than about 500 kPa;
   and, after an optional drying time;
   (2) applying to the skin on top of the film, a long-wear a cosmetic composition comprising at least one silicone-polyamide copolymer, at least one silicone film former, and at least one volatile oil.

3. The method of claim 1, wherein the at least one thermoplastic elastomer is present in the skin-tightening composition in an amount ranging from about 5% to about 25% by weight, relative to the total weight of the skin-tightening composition.

4. The method of claim 1, wherein the at least one adhesive polymer is chosen from polymer particles comprising about 80% to about 100%, by weight, of $C_1$-$C_4$ alkyl (meth)acrylate and of about 0% to about 20%, by weight, of ethylenically unsaturated acid monomer of $C_1$-$C_4$ alkyl (methacrylate) polymer in an oil dispersion.

5. The method of claim 1, wherein the polymer of the particles is chosen from:
   polymers consisting of at one or more $C_1$-$C_4$ alkyl(methacrylate)polymer; and
   polymers consisting essentially of a copolymer of $C_1$-$C_4$ (meth)acrylate and of (meth)acrylic acid or maleic anhydride.

6. The method of claim 1, wherein the skin-tightening composition further comprises at least one additional component chosen from silicone elastomers, water, and colorants.

7. The method of claim 1, wherein the skin-tightening composition further comprises at least one silicone elastomer chosen from silicone crosspolymers dispersed in at least one oil.

8. The method of claim 1, wherein the silicone film former of the long-wear cosmetic composition is chosen from silsesquioxane, polyalkylsilsesquioxane, polymethylsilsesquioxane, siloxysilicate, trialkylsiloxysilicate, and trimethylsiloxysilicate.

9. The method of claim 1, wherein the long-wear cosmetic composition is a makeup composition, a foundation, or a concealer composition.

10. The method of claim 1, wherein the ratio of thermoplastic elastomer:adhesive polymer in the skin-tightening composition is in the range of about 1:1 to 8:1.

11. The method of claim 1, wherein the skin-tightening composition has a consistency G* of greater than about 100 Pa (at 10% strain) and a phase angle below about 45°.

12. The method of claim 2, wherein the at least one thermoplastic elastomer is present in the skin-tightening composition in an amount ranging from about 5% to about 25% by weight, relative to the total weight of the skin-tightening composition.

13. The method of claim 2, wherein the at least one adhesive polymer is chosen from polymer particles comprising about 80% to about 100%, by weight, of $C_1$-$C_4$ alkyl (meth)acrylate and of about 0% to about 20%, by weight, of ethylenically unsaturated acid monomer of $C_1$-$C_4$ alkyl (methacrylate) polymer in an oil dispersion.

14. The method of claim 2, wherein the polymer of the particles is chosen from:
   polymers consisting of at one or more $C_1$-$C_4$ alkyl(methacrylate)polymer; and
   polymers consisting essentially of a copolymer of $C_1$-$C_4$ (meth)acrylate and of (meth)acrylic acid or maleic anhydride.

15. The method of claim 2, wherein the skin-tightening composition further comprises at least one additional component chosen from silicone elastomers, water, and colorants.

16. The method of claim 2, wherein the skin-tightening composition further comprises at least one silicone elastomer chosen from silicone crosspolymers dispersed in at least one oil.

17. The method of claim 2, wherein the silicone film former of the long-wear cosmetic composition is chosen from silsesquioxane, polyalkylsilsesquioxane, polymethylsilsesquioxane, siloxysilicate, trialkylsiloxysilicate, and trimethylsiloxysilicate.

18. The method of claim 1, wherein the long-wear cosmetic composition is a makeup composition, a foundation, or a concealer composition.

19. The method of claim 1, wherein the ratio of thermoplastic elastomer:adhesive polymer in the skin-tightening composition is in the range of about 1:1 to 8:1.

20. The method of claim 1, wherein the skin-tightening composition has a consistency G* of greater than about 100 Pa (at 10% strain) and a phase angle below about 45°.

* * * * *